US007666431B2

(12) United States Patent
Broder et al.

(10) Patent No.: US 7,666,431 B2
(45) Date of Patent: Feb. 23, 2010

(54) COMPOSITIONS AND METHODS FOR THE INHIBITION OF MEMBRANE FUSION BY PARAMYXOVIRUSES

(75) Inventors: Christopher C. Broder, Rockville, MD (US); Katharine N. Bossart, San Francisco, CA (US)

(73) Assignee: The Henry M. Jackson Foundation for the Advancement of Military Medicine, Inc., Rockville, MD (US)

( * ) Notice: Subject to any disclaimer, the term of this patent is extended or adjusted under 35 U.S.C. 154(b) by 195 days.

(21) Appl. No.: 10/528,800

(22) PCT Filed: Nov. 13, 2002

(86) PCT No.: PCT/US02/36283

§ 371 (c)(1),
(2), (4) Date: Mar. 31, 2006

(87) PCT Pub. No.: WO03/057824

PCT Pub. Date: Jul. 17, 2003

(65) Prior Publication Data

US 2006/0233821 A1    Oct. 19, 2006

Related U.S. Application Data

(60) Provisional application No. 60/331,231, filed on Nov. 13, 2001.

(51) Int. Cl.
*A61K 39/38* (2006.01)
*A61K 39/00* (2006.01)
*A61K 39/12* (2006.01)
*A61K 39/295* (2006.01)
*A61K 39/155* (2006.01)
*C07K 14/00* (2006.01)
*A61K 39/285* (2006.01)

(52) U.S. Cl. ............... 424/186.1; 424/185.1; 424/184.1; 424/202.1; 424/211.1; 530/300

(58) Field of Classification Search ........................ None
See application file for complete search history.

(56) References Cited

U.S. PATENT DOCUMENTS 5,843,451 A * 12/1998 Compans et al. ......... 424/192.1

OTHER PUBLICATIONS

Genbank Accession # AF212302, published 2001.*
Patch et al., Quantitative analysis of Nipah virus proteins released as virus-like particles reveals central role for the matrix protein, 2007, Virology Journal, vol. 4, No. 1, pp. 1-14.*
Holbrook et al., Animal models of highly pathogenic RNA viral infections: Encephalitis viruses, 2008, Antiviral Research, vol. 78, pp. 69-78.*
Mungall et al., Feline Model of Acute Nipah Virus Infection and Protection with a Soluble Glycoprotein-Based Subunit Vaccine, 2006, Journal of Virology, vol. 80, No. 24, pp. 12293-12302.*
Williamson et al., Experimental Hendra Virus Infection in Pregnant Guinea-pigs and Fruit Bats (*Pteropus poliocephalus*), 1999, Journal of Comparative Pathology, vol. 122, pp. 201-207.*
Harcourt et al., Molecular Characterization of Nipah Virus, a Newly Emergent Paramyxovirus, 2000, Virology, vol. 271, pp. 334-349.*
Bembridge et al., DNA encoding the attachment (G) or fusion (F) protein of respiratory syncytial virus induces protection in the absence of pulmonary inflammation, 2000, Journal of General Virology, vol. 81, pp. 2519-2523.*
Bossart et al., Membrane Fusion Tropism and Heterotypic Functional Activities of the Nipah Virus and Hendra Virus Envelope Glycoproteins, 2002, Journal of Virology, vol. 76, No. 22, pp. 11186-11198.*
Bossart et al. (2001). Functional Expression and Membrane Fusion Tropism of The Envelope Glycoproteins of Hendra Virus. Virology 290:121-135.
Chambers et al. (1990). Heptad repeat sequences are located adjacent to hydrophobic regions in several types of virus fusion glycoproteins. J. Gen. Virol. 71:3075-3080.
Chua et al. (2000). Nipah Virus: A Recently Emergent Deadly Paramyxovirus. Science 288:1432-1435.
Gosh et al. (1997). A Leucine Zipper Motif in the Ectodomain of Sendai Virus Fusion Protein Assembles in Solution and in Membranes and Specifically Binds Biologically-Active Peptides and the Virus. Biochemistry 36:15451-15462.
Harcourt et al. (2001). Molecular Characterization of Nipah Virus, a Newly Emergent Paramyxovirus. Virology 271:334-349.
Harcourt et al. (2001). Molecular Characterization of the Polymerase Gene and Genomic Termini of Nipah Virus. Virology 287:192-201.
Joshi et al. (1998). A Core Trimer of the Paramyxovirus Fusion Protein: Parallels to Influenza Virus Hemagglutinin and HIV-1 gp41. Virology 248:20-34.
Lambert et al. (1996). Peptides from conserved regions of paramyxovirus fusion (F) proteins are potent inhibitors of viral fusion. Proc. Natl. Acad. Sci. US 93:2186-2191.
Paterson et al. (1987). Comparison of the Relative Roles of the F and HN Surface Glycoproteins of the Paramyxovirus Simian Virus 5 in Inducing Protective Immunity. J. Virol. 61:1972-1977.

(Continued)

*Primary Examiner*—Gary B Nickol
*Assistant Examiner*—Benjamin P Blumel
(74) *Attorney, Agent, or Firm*—Morgan Lewis & Bockius LLP (57) ABSTRACT

Fusion of the membrane of enveloped viruses with the plasma membrane of a receptive host cell is a prerequisite for viral entry and infection and an essential step in the life cycle of all enveloped viruses, such as paramyxoviruses. The instant invention is directed to providing polypeptides which are a heptad portion of a Henipavirus F protein effective against fusion between a membrane of a paramyxovirus and a plasma membrane of a cell. The instant invention also provides nucleic acids, compositions, and methods effective against paramyxovirus infection. Accordingly, the instant invention provides therapeutic agents and vaccines effective against paramyxoviruses viruses, especially HeV or NiV.

12 Claims, 3 Drawing Sheets

OTHER PUBLICATIONS

Rapaport et al. (1995). A synthetic peptide corresponding to a conserved heptad repeat domain is a potent inhibitor of Sendai virus-cell fusion: an emerging similarity with functional domains of other viruses. EMBO 14: 5524-5531.

Wang et al. (2001) Molecular biology of Hendra and Nipah Viruses. Microbes and Infection 3:279-287.

Wild et al. (1997). Inhibition of measles virus infection and fusion with peptides corresponding to the leucine zipper region of the fusion protein. J. Gen. Virol. 78: 107-111.

Yao et al. (1997). Association of the Parainfluenza Virus Fusion and Hemagglutinin-Neuraminidase Glycoproteins on Cell Surfaces. J. Virol. 71:650-656.

Young et al. (1997). Analysis of Peptide Inhibitor of Paramyxovirus (NDV) Fusion Using Biological Assays, NMR, and Molecular Modeling. Virology 238: 291-304.

Young et al. (1999). Interaction of Peptides with Sequences from the Newcastle Disease Virus Fusion Protein Heptad Repeat Regions. J. Virol. 73: 5954-5956.

* cited by examiner

COMPOSITIONS AND METHODS FOR THE INHIBITION OF MEMBRANE FUSION BY PARAMYXOVIRUSES

REFERENCE TO RELATED APPLICATIONS

The present application is a U.S. National Phase Application of International Application PCT/US2002/036283, filed Nov. 13, 2002, which claims the benefit of U.S. Provisional Application No. 60/331,231 Nov. 13, 2001, the entire disclosures of which are hereby is incorporated by reference in their entireties.

RIGHTS IN THE INVENTION

This invention was made, in part, with support from the United States Government, grant no. RO73IL. Accordingly, the United States Government may have certain rights to this invention.

BACKGROUND OF THE INVENTION

1. Field of the Invention

This invention relates to peptides, compositions and methods involving these peptides for the inhibition of membrane fusion by paramyxoviruses and, in particular, membrane fusion mediated by Hendra virus and Nipah virus.

2. Description of the Background

Membrane fusion is a ubiquitous cell biological process. Fusion events which mediate cellular housekeeping functions, such as endocytosis, constitutive secretion, and recycling of membrane components, occur continuously in all eukaryotic cells.

Additional fusion events occur in specialized cells. Intracellularly, for example, fusion events are involved in such processes as occur in regulated exocytosis of hormones, enzymes and neurotransmitters. Intercellularly, such fusion events feature prominently in, for example, sperm-egg fusion and myoblast fusion.

Fusion events are also associated with disease states. For example, fusion events are involved in the formation of giant cells during inflammatory reactions, and particularly, the entry of all enveloped viruses into cells.

For example, the paramyxoviruses are negative-stranded RNA containing enveloped viruses encompassing a variety of important human and animal pathogens including measles virus (MeV), canine distemper virus (CDV), human parainfluenza viruses (hPIV) 1-4, and simian virus 5 (SV5) (reviewed in (Lamb and Kolakofsky, 1996)). These viruses contain two principal membrane-anchored glycoproteins which appear as spikes projecting from the envelope membrane of the viral particle when imaged in the electron microscope. One glycoprotein is associated with virion attachment to the host cell and, depending on the particular paramyxovirus, has been designated as either the hemagglutinin-neuraminidase protein (HN), the hemagglutinin protein (H), or the G protein which has neither hemagglutinating nor neuraminidase activities. The attachment glycoproteins of the paramyxoviruses are type II integral membrane proteins. In several cases where the attachment glycoprotein is of the HN type, it is sialic acid moieties which serve as receptors for virus entry. For paramyxoviruses possessing an H or G attachment glycoprotein the identity of host cell receptors are not known, except in the case of MeV where CD46 can serve as a functional receptor (Naniche et al., 1993). The second glycoprotein is the fusion protein (F), a type I membrane glycoprotein, which facilitates the membrane fusion event between the virion and host cell during virus infection (reviewed in Lamb, 1993).

Fusion of the membrane of enveloped viruses with the plasma membrane of a receptive host cell is a prerequisite for viral entry and infection and an essential step in the life cycle of all enveloped viruses. Following paramyxovirus attachment to a permissive host cell, fusion at neutral pH between the virion and plasma membranes ensues, resulting in delivery of the nucleocapsid into the cytoplasm (reviewed in (Lamb and Kolakofsky, 1996)). In a related process, cells expressing these viral glycoproteins at their surfaces can fuse with receptor-bearing cells, resulting in the formation of multinucleated giant cells (syncytia). The paramyxovirus F glycoprotein shares several features with other viral membrane fusion proteins, including the envelope glycoprotein of retroviruses like gp120/gp41 of HIV-1, and hemagglutinin (HA) of influenza virus (reviewed in (Hernandez et al., 1996)). The biologically active F protein consists of two disulfide linked subunits, $F_1$ and $F_2$, that are generated by the proteolytic cleavage of a precursor polypeptide known as $F_0$ (reviewed in (Klenk and Garten, 1994; Scheid and Choppin, 1974)). In all cases the membrane-anchored subunit contains a new amino terminus that is hydrophobic and highly conserved across virus families and referred to as the fusion peptide (reviewed in (Hunter, 1997)). The fusion peptide is an important structural element required to mediate virion/host cell membrane fusion. All paramyxoviruses studied to date, with the exception of SV5, under certain circumstances, require both the attachment and F glycoprotein for membrane fusion (Paterson, Johnson, and Lamb, 1997). Although evidence of physical interactions have only been rarely detected, it is hypothesized that the binding protein must somehow signal and induce a conformational change in F leading to virion/host cell membrane fusion (Lamb, 1993).

In 1994, a new paramyxovirus, now called Hendra virus (HeV) and recognized to be a member of the subfamily Paramyxovirinae, was isolated from fatal cases of respiratory disease in horses and humans, and was shown to be distantly related to MeV and other members of the morbillivirus genus (Murray et al., 1995). The first outbreak of severe respiratory disease in the Brisbane suburb of Hendra resulted in the death of 13 horses and their trainer, and the non-fatal infection of a stable hand and a further 7 horses. At approximately the same time, in an unrelated incident almost 100 km north of Hendra, a 35-year-old man experienced a brief aseptic meningitic illness after caring for and assisting at the necropsies of two horses subsequently shown to have died as a result of HeV infection. Thirteen months later the man suffered severe encephalitis characterized by uncontrolled focal and generalized epileptic-activity. A variety of studies that were performed in the evaluation of this fatality, including serology, PCR, electron microscopy and immunohistochemistry, strongly suggested that HeV was indeed the cause of this patient's encephalitis, and the virus was acquired from the HeV-infected horses (O'Sullivan et al., 1997). In all, fifteen horses and two people died in the two episodes. At the time the source of the emerging virus was undetermined, but more recently it has been found that approximately 50% of Australian fruit bats, commonly known as flying foxes, have antibodies to HeV and HeV-like viruses have been isolated from bat uterine fluids and it appears that these animals are the natural host for the virus (Field et al., 2001; Halpin et al., 1999; Halpin et al., 2000; Young et al., 1996).

More recently, the nucleic acid sequence of the genes of HeV has been compared with those of other paramyxoviruses (Wang et al., 1998; Yu et al., 1998a; Yu et al., 1998b). These later studies have confirmed that HeV is a member of the Paramyxoviridae, subfamily Paramyxovirinae, but low homology with other subfamily members and the presence of several novel biological and molecular features such as F protein cleavage at a single lysine residue and genome length suggest classification in a new genus within the Paramyxovirinae.

Subsequent to these events, an outbreak of severe encephalitis in people with close contact exposure to pigs in Malaysia and Singapore occurred in 1998 (Anonymous, 1999). The outbreak was first noted in late September 1998 and by mid-June 1999, more than 265 cases of encephalitis, including 105 deaths, had been reported in Malaysia, and 11 cases of encephalitis or respiratory illness with one death had been reported in Singapore. This may represent a near 40% fatality rate upon infection, because the incidence of subclinical human infections during these episodes has not been well defined. Electron microscopic, serologic, and genetic studies have since indicated that this virus also belongs to the Paramyxovirinae subfamily, and was most closely related to HeV. This virus was named Nipah virus (NiV) after the small town in Malaysia from which the first isolate was obtained from the cerebrospinal fluid of a fatal human case (Chua et al., 2000; Chua et al., 1999; Goh et al., 2000; Lee et al., 1999; Lim et al., 2000). NiV and HeV are now recognized as the prototypic members of a new genus within the Paramyxovirinae subfamily called Henipavirus (Wang et al., 2001; Wang and Eaton, 2001). Both HeV and NiV are unusual among the paramyxoviruses in their ability to infect and cause potentially fatal disease in a number of host species, including humans and in that they have an exceptionally large genome.

These viruses classified as Biosafety Level 4 agents (BSL-4) and have the potential to be used as biological warfare agents. There are no existing antiviral therapies effective against these viruses, and the only therapies in existence to any viruses in the paramyxovirus family are attenuated vaccines for the prevention of infection by MeV and Mumps virus. Accordingly, agents and compositions effective against infections by viruses in the paramyxovirus family are particularly desirable. In this connection, the heptad peptides of the instant invention represent an effective therapy for paramyxovirus infection resulting from, e.g., a biological weapon, a natural outbreak, or a BSL-4 laboratory accident.

SUMMARY OF THE INVENTION

The present invention overcomes the problems and disadvantages associated with current strategies and designs and provides effective treatments against infection by a paramyxovirus of the subfamily Henipavirus.

One embodiment of the invention is directed to peptides and compositions containing peptides that are useful for treating infection by viruses of the subfamily Henipavirus by inhibiting membrane fusion induced by HeV and NiV. Such peptides comprise the amino acid sequence of the F glycoprotein of Henipaviruses and preferably the heptad peptide of the C-terminal region. Most preferably the peptide is SEQ ID NO 1 or SEQ ID NO 2. This embodiment further comprises nucleic acids the encode peptides of the invention.

Another embodiment of the invention is directed to methods for the treatment of infection by viruses of the subfamily Henipavirus by administering peptides of the invention to a patient.

Another embodiment of the invention is directed to antibodies to peptides of the invention and diagnostics containing these antibodies.

In another embodiment, the invention provides a recombinant or isolated polypeptide comprising a heptad portion of a Henipavirus F protein and biologically active fragments thereof and variants thereof.

Preferably, the polypeptide comprises the polypeptide sequence of selected from the group consisting of SEQ ID NO 1, SEQ ID NO 2, biologically active fragments thereof, and variants thereof. Preferably, the polypeptide functions to inhibit fusion of a membrane of a paramyxovirus and a plasma membrane of a cell. Preferably, the heptad portion is derived from HeV or NiV.

In another embodiment, the invention provides a pharmaceutical composition comprising an effective amount of a polypeptide sequence of selected from the group consisting of SEQ ID NO 1, SEQ ID NO 2, biologically active fragments thereof, and variants thereof, and a pharmaceutically acceptable carrier. In one embodiment, the composition is a therapeutic or post-exposure prophylactic. Preferably, the composition is in the form of a vaccine.

In another embodiment, the invention provides a method for inhibiting fusion between a membrane of a paramyxovirus and a plasma membrane of a cell comprising administering a composition according to the instant Preferably, the paramyxovirus is of the genus Henipavirus. Preferably, the paramyxovirus is of the subfamily Paramyxovirina. Preferably, paramyxovirus is HeV or NiV.

In another embodiment, the invention provides an isolated polynucleotide sequence encoding a polypeptide that inhibits fusion between a membrane of a paramyxovirus and a plasma membrane of a cell, wherein said polynucleotide is either a DNA sequence encoding a polypeptide of SEQ ID NO 1; and a DNA sequence capable of hybridizing under high stringency conditions to the complement of (a).

In another embodiment, the invention provides a vector comprising a polynucleotide sequence of the instant invention.

In another embodiment, the invention provides a cell comprising a polynucleotide sequence of the instant invention.

In another embodiment, the invention provides a method for treating infection with a virus, comprising administering a composition according the instant invention.

In another preferred embodiment. The instant invention provides aptamers of peptides of the instant invention and methods of using the same.

Other features and advantages of the invention will become apparent from the following description. It should be understood, however, that the description and the examples are given for illustration, and various changes and modifications within the spirit and scope of the invention will become apparent to those skilled in the art from this description.

DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment provided herein, serve to explain the principles of the invention. Thus, for a more complete understanding of the present invention, the objects and advantages thereof, reference is now made to the following descriptions taken in connection with the accompanying drawings in which:

FIG. 1(A) Representation of the HeV F glycoprotein depicting important structural and functional elements. (B) Amino acid sequence of the C-terminal heptad repeat of HeV F (SEQ ID NO: 1). (C) Helical wheel representation of the N- and C-terminal heptad repeats of HeV F (SEQ ID NOS 4-10, respectively in order of appearance from the top left clockwise and SEQ ID NOS 11 and 12 on the right.

DESCRIPTION OF THE INVENTION

As embodied and broadly described herein, the present invention is directed to effective treatments against infection by a paramyxovirus. More specifically, the present invention relates to peptides that are useful at inhibiting membrane fusion induced by viruses of the subfamily Henipavirus such as, for example, HeV and NiV.

Understanding the mechanisms of how paramyxoviruses emerge, mediate host cell infection and cross species, is an important step towards determining how to address such new, emerging, and sometimes reemerging infectious disease threats. To this end, examination of HeV was begun with the characterization and use of the virus' envelope glycoproteins that facilitate attachment and membrane fusion events during infection. HeV possesses a F glycoprotein, similar to other paramyxoviruses, that likely mediates membrane fusion. The attachment glycoprotein has been designated G, like that of respiratory syncytial virus, because, on the basis of genetic analyses and observations with infectious virus, HeV contains neither hemagglutinating nor neuraminidase activity (Murray et al., 1995), suggesting that the cellular receptor may not be sialic acid (Yu et al., 1998a).

All viral membrane glycoproteins that are the mediators of membrane fusion, virion attachment or both, are invariably oligomeric (Doms et al., 1993). Considerable advances in the understanding of the structural features of these oligomeric viral envelope glycoproteins has been attained in recent years and have centered on the influenza virus and Human Immunodeficiency virus (HIV) systems. A notable structural feature of many of these fusion glycoproteins is the presence of 2 α-helical domains referred to as heptad repeats that are important for both oligomerization and function of the glycoprotein, where they are involved in the formation of a trimer-of-hairpins structure (Hughson, 1997; Singh, Berger, and Kim, 1999). Peptides corresponding to either of these domains can potently inhibit the fusion process, first noted with sequences derived from the gp41 subunit of HIV-1 envelope glycoprotein (Jiang et al., 1993; Wild et al., 1994). Inhibition of the formation of the trimer-of-hairpins structure inhibits the fusion process, and this mechanism has been modeled and described by several groups (Chan and Kim, 1998; Munoz-Barroso et al., 1998; Rimsky, Shugars, and Matthews, 1998; Root, Kay, and Kim, 2001). Indeed, the development and clinical application of fusion-inhibitors, as antiviral therapies for HIV-1, has been a direct result from this area of research. Recently, an α-helical trimeric core complex has been defined in the F protein of Simian virus 5 (SV5) and is also believed to be either the fusion competent structure or the structure formed after fusion has occurred, analogous to HIV-1 gp41 (Lamb, Joshi, and Dutch, 1999). In addition, peptide sequences from the C-terminal heptad of SV5 F, as well as Measles virus (MeV) F, have been shown to be potent inhibitors of membrane fusion (Joshi, Dutch, and Lamb, 1998; Wild and Buckland, 1997).

Figure 1:
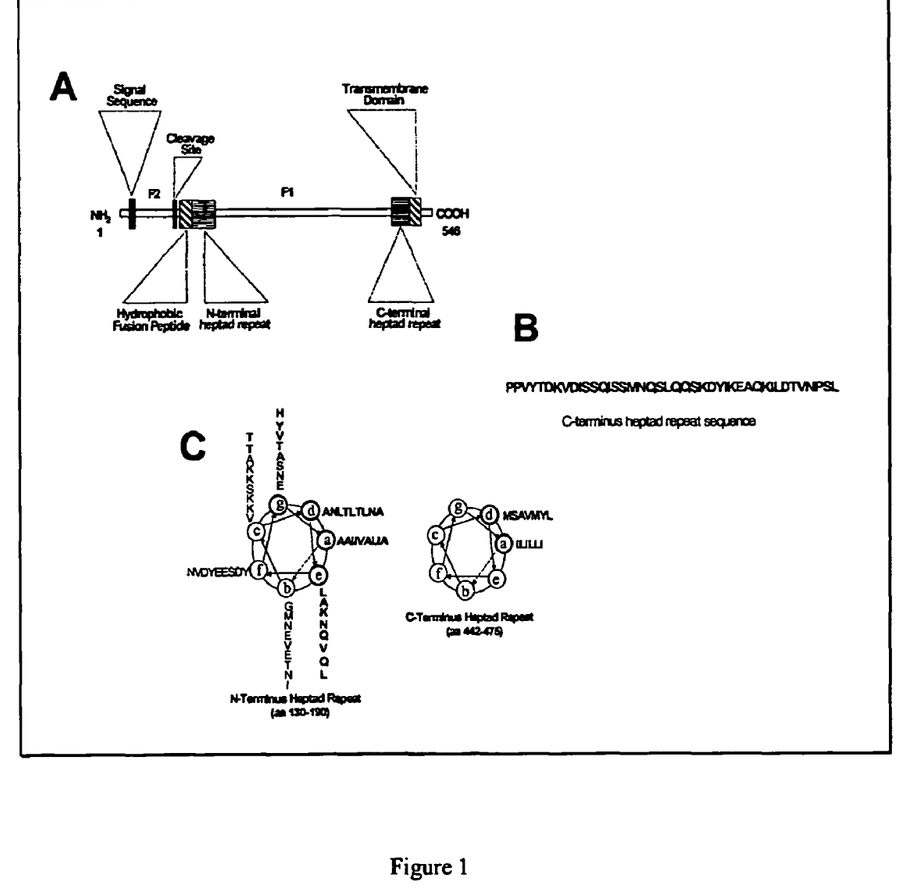
Figure 2:
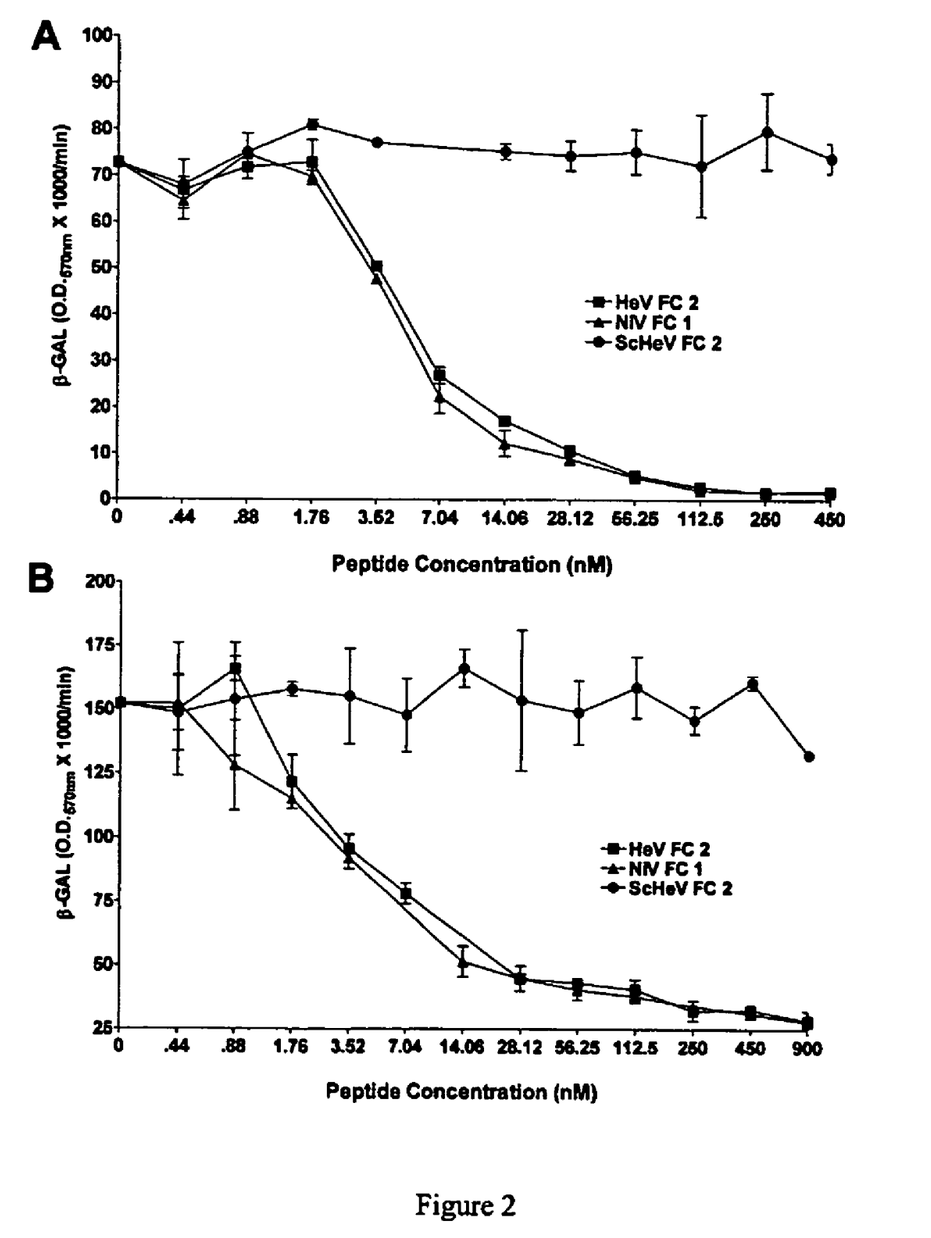
FIG. 2 Graphs of β-gal activity verses increasing peptide concentration. A: Inhibition of HeV-mediated fusion by C-terminal synthetic F peptides. B: Inhibition of NiV-mediated fusion by C-terminal synthetic F peptides.

Heptad repeats of Hendra virus (HeV) and Nipah virus (NiV) F were analyzed using helical wheel diagrams and sequences were identified that may inhibit virus-mediated fusion (FIG. 1). Next, the specificity of recombinant HeV fusion system was tested using a synthetic 42 amino acid peptide (FC1) corresponding to the HeV F C-terminal heptad. It was surprisingly discovered that the FC1 peptide could completely inhibit HeV-mediated fusion in the nM range (FIG. 2). It is believed this peptide will also inhibit live HeV infection when tested under BSL-4 conditions, and represents a therapeutic avenue for both HeV and NiV infections. Indeed, the HeV F C-terminal heptad peptide was also capable of inhibiting recombinant NiV-mediated fusion at slightly lower efficiencies likely due to several mismatches in the heptad sequence. The exact NiV C-terminal heptad peptide is being synthesized and tested. The use of such peptide inhibitors to HeV and NiV may be the only effective therapy during acute encephalitic episodes caused by infection with these agents in either humans or livestock such as valuable race horses or polo ponies.

In one embodiment, the invention is directed to compositions containing all or effective portions of a peptide corresponding to the F protein of Henipavirus. Preferably, the peptide is the C-terminal heptad peptide of HeV, which has been localized to position 442 to 489 of the F glycoprotein. This peptide has been shown to significantly reduce membrane fusion of HeLa cells infected with recombinant vaccinia virus containing HeV F and G proteins. Other viruses of the subfamily Henipavirus, including those yet to be discovered, that have a corresponding region in their F protein, such as, for example, NiV F protein, are also effective at inhibiting membrane fusion and as a treatment against infection. Compositions are effective both in vitro and also in vivo in the treatment and prevention of infection by Henipavirus in cells or in mammals such as, for example, horses, sheep, pigs, cattle and humans. Compositions may contain only peptide of the invention or additional ingredients such as pharmaceutically acceptable agents including carbohydrates, saccharides, polysaccharides, lipids, fatty acids, proteins or protein fragments, glycol, polyethylene glycol, glycerol, glucose, oil, water, cellulose, and other similar substances. Preferably, peptides are physiologically stable in the cells or patient for an time sufficient for the effective inhibition of membrane fusion.

The instant proteins, peptides and polypeptides describe any chain of amino acids, regardless of length or post-translational modification (for example, glycosylation or phosphorylation) and apply to amino acid polymers in which one or more amino acid residue is an artificial chemical mimetic of a corresponding naturally occurring amino acid. Thus, the instant polypeptides include full-length, naturally occurring proteins as well as recombinantly or synthetically produced polypeptides that correspond to a full-length naturally occurring protein or to particular domains or portions of a naturally occurring protein. The polypeptides also encompass mature proteins which have an added amino-terminal methionine to facilitate expression in prokaryotic cells.

The invention includes biologically active polypeptides and biologically active fragments thereof which refers to the ability to inhibit fusion between a membrane of a paramyxovirus and a plasma membrane of a host cell.

The present invention contemplates modification of the instant polypeptides to create variants. Such modifications may be deliberate, as by site-directed mutagenesis, or may be spontaneous. All of the polypeptides produced by these modifications are included herein as long as the ability to inhibit fusion between a membrane of a paramyxovirus and a plasma membrane of a host cell is present.

For example, the present invention contemplates the deletion of one or more amino acids from the instant polypeptides to create deletion variants. This deletion can be of one or more amino or carboxy terminal amino acids or one or more internal amino acids (e.g. silent substitutions or mutations). The present invention further contemplates one or more amino acid substitutions to the instant polypeptides to create subsititutional variants. The present invention contemplates that such substitutional variants would contain certain functional alterations, such as stabilizing against proteolytic cleavage. Yet, it is understood that such variants retain their inhibitory activity.

Substitutions preferably are conservative, that is, one amino acid is replaced with one of similar shape and charge. Conservative substitutions are well known in the art and include, for example, the changes of: alanine to serine; arginine to lysine; asparigine to glutamine or histidine; aspartate to glutamate; cysteine to serine; glutamine to asparigine; glutamate to aspartate; glycine to proline; histidine to asparigine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Other substitutions are routine or well known in the art and are well within the scope of the instant invention.

The present invention further contemplates the insertion of one or more amino acids to the instant polypeptides sequences to create an insertional variant. Examples of such insertional variants include fusion proteins such as those used to allow rapid purification of the polypeptide and also can include hybrid polypeptides containing sequences from other proteins and polypeptides which are homologues of the inventive polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptides. These typically are smaller insertions than the fusion proteins described above and are introduced, for example, to disrupt a protease cleavage site.

Polypeptides of the present invention can be synthesized by such commonly used methods as t-BOC or FMOC protection of alpha-amino groups. Both methods involve stepwise syntheses whereby a single amino acid is added at each step starting from the C terminus of the peptide (Coligan et al., Current Protocols in Immunology, Wiley Interscience, Unit 9, 1991). In addition, polypeptide of the present invention can also be synthesized by solid phase synthesis methods (e.g., Merrifield, J. Am. Chem. Soc. 85:2149, 1962; and Steward and Young, Solid Phase Peptide Synthesis, Freeman, San Francisco pp. 27-62, 1969) using copolyol (styrene-divinylbenzene) containing 0.1-1.0 mM amines/g polymer. On completion of chemical synthesis, the polypeptides can be deprotected and cleaved from the polymer by treatment with liquid HF 10% anisole for about 15-60 min at 0° C. After evaporation of the reagents, the peptides are extracted from the polymer with 1% acetic acid solution, which is then lyophilized to yield crude material. This can normally be purified by such techniques as gel filtration of Sephadex G-15 using 5% acetic acid as a solvent. Lyophilization of appropriate fractions of the column will yield a homogeneous polypeptide or polypeptide derivatives, which are characterized by such standard techniques as amino acid analysis, thin layer chromatography, high performance liquid chromatography, ultraviolet absorption spectroscopsy, molar rotation, solubility and quantitated by solid phase Edman degradation.

The instant polypeptides include their pharmacologically acceptable salts by treatment with physiologically acceptable acids or bases. These salts include, for example, salts with an inorganic acid such as hydrochloric acid, sulfuric acid and nitric acid and, depending on the compounds, salts with an organic acid such as acetic acid, nitric acid, succinic acid and maleic acid, salts with an alkali metal such as sodium and potassium, and salts with an alkaline earth metal such as calcium. The instant polypeptides also include all their stereoisomeric forms including their diastereomers.

In a preferred embodiment, the invention is directed to nucleic acids that encode peptides of the invention. These may comprise DNA, RNA or PNA and contain sequences in addition to sequences that encode the peptide. Such additional sequences may include transcription or translation controlling sequences such as promoter or operator sequences, transcription initiation sites, splice junctions, termination sites, origins of replication and other control sequences. Preferably, the nucleic acid is an expression vector that allows for the controlled expression (e.g. inducible expression) of the encoded peptide. Suitable vectors include eukaryotic vectors such as viral vectors, prokaryotic vectors such as plasmids, and shuttle vectors.

The instant polynucleotide is a polymer of deoxyribonucleotides or ribonucleotides in the form of a separate fragment or as a component of a larger construct In a preferred embodiment, the invention provides a DNA sequence encoding a polypeptide of SEQ ID NO 1 or SEQ ID NO 2; and DNA sequence capable of hybridizing under high stringency conditions to the complement of a DNA sequence encoding a polypeptide of SEQ ID NO 1 or SEQ ID NO 2.

Polynucleotide sequences of the invention include DNA, RNA and cDNA sequences. Preferably, the polynucleotide sequences encoding the instant polypetides is the sequence of SEQ ID NO 1 or SEQ ID NO 2. DNA sequences of the present invention can be obtained by several methods. For example, the DNA can be isolated using hybridization procedures which are known in the art. Such hybridization procedures include, for example, hybridization of probes to cDNA libraries to detect shared nucleotide sequences, antibody screening of expression libraries to detect shared structural features, such as a common antigenic epitope, and synthesis by the polymerase chain reaction (PCR), or synthetic chemical synthesis of the instant polypeptide sequence.

Hybridization procedures are useful for screening of recombinant clones by using labeled mixed synthetic oligonucleotide probes, wherein each probe is potentially the complete complement of a specific DNA sequence in a hybridization sample which includes a heterogeneous mixture of denatured double-stranded DNA. For such screening, hybridization is preferably performed on either single-stranded DNA or denatured double-stranded DNA. Hybridization is particularly useful for detection of cDNA clones derived from sources where an extremely low amount of mRNA sequences relating to the polypeptide of interest are present. Using stringent hybridization conditions directed to avoid non-specific binding, it is possible to allow an autoradiographic visualization of a specific cDNA clone by the hybridization of the target DNA to that single probe in the mixture, which is its complement (Wallace et al. Nucl. Acid Res. 9:879, 1981). Stringent conditions preferably include high stringency conditions. See, for example, Maniatis et al, Molecular Cloning (A Laboratory Manual), Cold Spring Harbor Laboratory, pages 387-389, 1982. One such high stringency hybridization condition is, for example, 4×SSC at 65° C., followed by washing in 0.1×SSC at 65° C. for thirty minutes. Alternatively, another high stringency hybridization condition is in 50% formamide, 4×SSC at 42° C.

The development of specific DNA sequences encoding the instant polypeptides can also be obtained by isolation of double-stranded DNA sequences from the genomic DNA, chemical manufacture of a DNA sequence to provide the necessary codons for the polypeptide of interest, and in vitro synthesis of a double-stranded DNA sequence by reverse transcription of mRNA isolated for a eukaryotic donor cell. In the latter case, a double-stranded DNA complement of mRNA is eventually formed which is generally referred to as cDNA.

The synthesis of DNA sequences is frequently a method that is preferred when the entire sequence of amino acids residues of the desired polypeptide product is known. When the entire sequence of amino acid residues of the desired polypeptide is not known, direct synthesis of DNA sequences is not possible and it is desirable to synthesize cDNA sequences. cDNA sequence isolation can be done, for example, by formation of plasmid- or phage-carrying cDNA libraries which are derived from reverse transcription of mRNA. mRNA is abundant in donor cells that have high levels of genetic expression. In the event of lower levels of expression, PCR techniques are preferred. When a significant portion of the amino acid sequence is known, production of labeled single or double stranded DNA or RNA probe sequences duplicating a sequence putatively present in the target cDNA may be employed in DNA/DNA hybridization procedures, carried out on cloned copies of the cDNA (denatured into a single-stranded form) (Jay et al., Nucl. Acid Res. 11:2325, 1983).

The polynucleotides of this invention include sequences that are degenerate as a result of the genetic code. The genetic code is described as degenerate because more than one nucleotide triplet, called a codon, can code for a single amino acid. The present invention contemplates the degeneracy of the genetic code and includes all degenerate nucleotide sequences which encode.

The present invention further includes allelic variations, i.e., naturally-occurring base changes in a species population which may or may not result in an amino acid change, to the polynucleotide sequences encoding a polypeptide of SEQ ID NO 1 or SEQ ID NO 2; and DNA sequence capable of hybridizing under high stringency conditions to the complement of a DNA sequence encoding a polypeptide of SEQ ID NO 1 or SEQ ID NO 2. The inventive polynucleotide sequences further comprise those sequences which hybridize under high stringency conditions (see, for example, Maniatis et al, Molecular Cloning (A Laboratory Manual), Cold Spring Harbor Laboratory, pages 387-389, 1982) to the coding regions or to the complement of the coding regions of a polypeptide of SEQ ID NO 1. One such high stringency hybridization condition is, for example, 4×SSC at 65° C., followed by washing in 0.1×SSC at 65° C. for thirty minutes. Alternatively, another high stringency hybridization condition is in 50% formamide, 4×SSC at 42° C.

The instant vector is a DNA molecule, such as a plasmid, cosmid, or bacteriophage that has the capability of replicating autonomously in a host cell. Cloning vectors may preferably contain (i) one or a small number of restriction endonuclease recognition sites at which foreign DNA sequences can be inserted in a determinable fashion without loss of an essential biological function of the vector, and (ii) a marker gene that is suitable for use in the identification and selection of cells transformed with the cloning vector. Marker genes may typically include genes that provide tetracycline resistance or ampicillin resistance.

The cell is a naturally occurring cell or a transformed cell that contains an expression vector and supports the replication or expression of the expression vector. Host cells may be cultured cells, explants, cells in vivo, and the like. Host cells may be prokaryotic cells such as $E.\ coli$, or eukaryotic cells such as yeast, insect, amphibian, or mammalian cells such as CHO, HeLa, and the like.

In a preferred embodiment, the invention is directed to methods for administering peptides of the invention for inhibiting membrane fusion induced by a paramyxovirus. Membrane fusion is the process whereby the lipid envelope of the virus fuses with the plasma membrane of the host cell. In vivo this is an essential step in infection. In vitro, the process is referred to as syncytial cell formation whereby the plasma membranes of a plurality of cells combine to form one or more syncytia.

The instant pharmaceutical compositions can also be administered orally or non-orally in the form of, for example, granules, powders, tablets, capsules, syrup, suppositories, injections, emulsions, elixir, suspensions or solutions, by mixing these effective components, individually or simultaneously, with pharmaceutically acceptable carriers, excipients, binders, diluents or the like. In the case of formulating the effective components individually, while thus individually formulated agents can be administered in the form of their mixture prepared by using, for example, a diluent when administered, the individually formulated agents can also be administered separately or simultaneously or with time intervals to the one and same subject.

The instant pharmaceutical compositions of the present invention can be formulated in accordance with conventional procedures. In the present specification, "non-orally" include subcutaneous injection, intravenous injection, intramuscular injections, intraperitoneal injection or instillation. Injectable preparations, for example, sterile injectable aqueous suspensions or oil suspensions can be prepared by known procedure in the fields concerned, using a suitable dispersant or wetting agent and suspending agent. The sterile injections may be in the state of, for example, a solution or a suspension, which is prepared with a non-toxic diluent administrable non-orally, e.g. an aqueous solution, or with a solvent employable for sterile injection. Examples of usable vehicles or acceptable solvents include water, Ringer's solution and an isotonic aqueous saline solution. Further, a sterile non-volatile oil can usually be employed as solvent or suspending agent.

Any non-volatile oil and a fatty acid can be used for this purpose, which includes natural or synthetic or semi-synthetic fatty acid oil or fatty acid, and natural or synthetic or semi-synthetic mono- or di- or tri-glycerides.

Rectal suppositories can be prepared by mixing the drug with a suitable non-irritable vehicle, for example, cocoa butter and polyethylene glycol, which is in the solid state at ordinary temperatures, in the liquid state at temperatures in intestinal tubes and melts in rectum to release the drug.

As a solid formulation for oral administration, the instant invention contemplates, for example, powders, granules, tablets, pills and capsules. The active component compounds can be mixed with at least one additive, for example, sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. These formulations can contain, as in conventional cases, further additives, for example, an inactive diluent, a lubricant such as magnesium stearate, a preservative such as paraben or sorbic acid, an anti-oxidant such as ascorbic acid, α-tocopherol or cysteine, a disintegrator, a binder, a thickening agent, a buffer, a sweetener, a flavoring agent and a perfuming agent. Tablets and pills can further be prepared with enteric coating. Examples of liquid preparations for oral administration include pharmaceutically acceptable emulsions, syrups, elixirs, suspensions and solutions, which may contain an inactive diluent, for example, water, which is conventionally employed in the field concerned.

The pharmaceutical composition of this invention may be used as a medicine for animals, such as mammals (e.g. human being, horse, cattle, sheep, dog, rabbit, mouse, etc.), preferably humans.

In a preferred embodiment, the instant invention provides a method for treating infection with a virus, preferably paramyxoviruses, comprising administering an effective amount of a composition of the preferred embodiment. In another preferred embodiment, the invention provides a method for inhibiting fusion between a membrane of a paramyxovirus and a plasma membrane of a cell comprising administering a composition according to the instant invention. These methods include the alleviation of symptoms associated with viral infection.

The effective amount is that amount which effectively inhibits fusion between a membrane of a paramyxovirus and a plasma membrane of a cell, or that which alleviates the symptoms of paramyxovirus infection. The effective amount is dependent on the age, body weight, general health conditions, sex, diet, dose interval, administration routes, excretion rate, combinations of drugs and conditions of the diseases treated, while taking these and other necessary factors into consideration.

Biologically active fragments are those which can inhibit fusion between a membrane of a paramyxovirus and a plasma membrane of a cell. This may be easily determined by a cell fusion assay. A cell fusion assay may be utilized to test the peptides' ability to inhibit viral-induced syncytia formation in vitro. Such an assay is illustrated in the examples below, and may comprise culturing uninfected cells in the presence of cells chronically infected with a syncytial-inducing virus and a peptide to be assayed. For each peptide, a range of peptide concentrations may be tested. This range should include a control culture wherein no peptide has been added. Standard conditions for culturing, well known to those of ordinary skill in the art, are used. After incubation for an appropriate period the culture is examined for the presence of multinucleated giant cells, which are indicative of cell fusion and syncytia formation.

Another embodiment of the invention is directed to antibodies specifically reactive to isolated peptides of the invention. Antibodies may be monoclonal or polyclonal, as desired, and may be of any isotype such as IgA, IgD, IgE, IgG, or IgM. Antibodies may be useful for treatment by interfering with interaction between Henipavirus and a cell and thereby preventing infection. Also, antibodies may be useful as a diagnostic for possible or suspected Henipavirus infection by detecting the presence of F glycoprotein in a sample obtained from the patient. Alternatively, diagnostic kits may comprise peptides of the invention and be used to detect circulating antibodies.

In another preferred embodiment, the instant invention also provides aptamers of peptides of the instant invention and methods for inhibiting fusion between a membrane of a paramyxovirus and a plasma membrane with the instant aptamers. The instant aptamers are peptide or nucleic acid molecules that are capable of binding to a protein or other molecule, or mimic the three dimensional structure of the active portion of the peptides of the invention, and thereby disturb the protein or other molecule function. The instant aptamers are based on heptad portion of a Henipavirus F protein and functions to inhibit fusion of a membrane of a paramyxovirus and a plasma membrane of a cell. Aptamers may be prepared by any known method, including synthetic, recombinant, and purification methods (*Nature* 1996 Apr. 11; 380(6574):548-50).

The present invention, thus generally described, will be understood more readily by reference to the following examples, which are provided by way of illustration and are not intended to be limiting of the present invention.

The following examples are offered to illustrate embodiments of the invention, but are not to be viewed as limiting the scope of the invention.

EXAMPLES

Nipah virus (NiV) and Hendra virus (HeV) are viruses that resulted in previously unrecognized fatal diseases in animals and humans. Nipah virus and Hendra virus are closely related members of a new genus, Henipavirus within the family Paramyxoviridae, a diverse group of large, enveloped, negative-sense single stranded RNA viruses, and include a variety of important human and animal pathogens. The recent emergence and discovery of these two viruses appears to have been the result of exposure of new hosts precipitated by certain economical, environmental, or behavioral changes. Hendra virus was identified first, from cases of severe respiratory disease that fatally affected both horses and man. Subsequent to that appearance, an outbreak of severe febrile encephalitis associated with human deaths occurred in Malaysia. Later studies identified a Hendra-like virus, now known as Nipah virus, as the etiologic agent of that episode. These viruses are unusual among the paramyxoviruses in their abilities to infect and cause potentially fatal disease in a number of host species, including humans, and are zoonotic Biological Safety Level-4 (BSL4) agents. Presently, the cat appears to be the ideal small animal model capable of reproducing the pathology seen in Nipah virus infected humans. Nipah and Hendra virus possess several biological features which make them highly adaptable for their use as biowarfare agents and are select agents of biodefense importance. The development of effective therapies or vaccines for these agents is critical.

The instant polypeptides are derived from the carboxyl (C)-terminal c-helical heptad repeat region of the NiV and HeV fusion glycoprotein (F), and block the virus-mediated fusion step by interfering with the formation of a trimer-of-hairpins structure in the fusion glycoprotein, which has been similarly demonstrated in a number of viral systems that possess a pH-independent mode of membrane fusion. In the absence of any passive or active immunization procedures or products to NiV and HeV, as well as no available anti-viral drugs for paramyxoviruses in general; the instant polypeptides developed here may well represent an effective therapy for NiV and HeV infection resulting from their use as a biological weapon, a natural outbreak, or a BSL4 laboratory accident.

The instant polypeptides are an effective therapeutic treatment for both NiV and HeV infection in animals and humans, such that acute encephalitic disease or death, may be prevented. The protective mechanism of the instant polypeptides will be to afford the virus-infected host an opportunity to mount a sterilizing immune response.

Example 1

The location of HeV F glycoprotein heptad repeats is shown in FIG. 1. A diagram of the HeV F glycoprotein depicting important structural and functional elements is depicted in FIG. 1A. Amino acid sequence of the C-terminal heptad repeat of HeV F (SEQ ID NO 1) is depicted in FIG. 1B. A helical wheel representation of the N- and C-terminal heptad repeats of HeV F is depicted in FIG. 1C. The bold-faced points on the helical wheel indicate important residue locations on the helix structure of the F protein of SV5 that mediate protein-protein interactions (Joshi, Dutch, and Lamb, 1998). The point "a" of one N-terminal heptad is thought to interact with point "d" of another SV5 F N-terminal heptad in an antiparallel orientation. Point "e" of the N-terminal heptad is thought to interact with point "a" of the C-terminal heptad, and point "g" of the N-terminal heptad is believed to interact with point "d" of the C-terminal heptad. In all, it is thought that three N-terminal heptad repeats and three C-terminal heptad repeats of three SV5 F proteins mediate the necessary protein-protein interactions that stabilize the fusogenic SV5 F trimer formation. Enlarged underlined amino acids represent HeV F residues that are identical to those found in the N- and C-terminal heptad repeats of SV5, enlarged but not underlined amino acids are hydrophobic conservative substitutions in HeV F as compared to SV5 F.

Example 2

Specific Heptad Peptide Inhibition of NiV and HeV-Mediated Membrane Fusion and Virus Infection To further assess the specificity and utility of the fusion system, ways were sought to specifically inhibit the cell-fusion process. Sequences which formed a trimer-of-hairpins structure whose oligomeric coiled-coil formation is mediated by the 2 α-helical heptad repeat domains of the fusion protein were investigated first. Peptides derived from either of the α-helical heptad repeat regions of enveloped viral fusion proteins are potentially potent inhibitors of the fusion process for a number of viruses. There are 2 putative α-helical domains in the HeV F glycoprotein. One HeV F heptad domain is proximal to the fusion peptide of $F_1$ (N-terminal heptad repeat), and the other is very close to the predicted transmembrane domain of $F_1$ (C-terminal heptad repeat). Helical wheel analysis of HeV F revealed a high degree of sequence homology of important functional residues with the heptad repeats of SV5 F, and both HeV and NiV have two putative heptad repeat domains in F. To determine if these domains played important roles in NiV and HeV-mediated fusion, a 42 amino acid peptide analogous to the NiV F C-terminus heptad repeat was synthesized (NiV FC1) and tested for its ability to interfere with NiV-mediated fusion. Since there were three amino acid differences within the C-terminus heptad repeat of HeV and NiV, a second peptide corresponding to the HeV F C-terminus heptad repeat was also synthesized (HeV FC2). A scrambled version of HeV FC2 was synthesized and used as a negative control (Table 1).

Specificity of NiV and HeV-mediated fusion was determined. Briefly, HeLa cells were infected with vaccinia recombinants encoding NiV or HeV F and G. Human U373 cells were infected with the *E. coli* LacZ-encoding reporter vaccinia virus vCB21R (target cells). Peptides were diluted and added to the glycoprotein-expressing cells. Cell populations were mixed and cell fusion was measured. Each peptide and serum concentration was performed in duplicate. Shown in FIGS. 2A and 2B are the results obtained in the presence of these peptides for both HeV and NiV-mediated fusion.

TABLE 1

Synthetic peptides corresponding to HeV and NiV F

| Peptide | Sequence | Target |
|---|---|---|
| HeV-FC2 SEQ ID NO 1 | PPVYTDKVDISSQISSMNQSL QQSKDYIKEAQKILDTVNPSL | C-terminal Heptad repeat |
| NiV-FC1 SEQ ID NO 2 | PPVFTDKVDISSQISSMNQSL QQSKDYIKEAQRLLDTVNPSL | C-terminal Heptad repeat |
| ScHeV FC2 SEQ ID NO: 3 | KPYTQSDVSMISLQSQKSINS LPSQIKDYVQKTVILAEDNP | Scrambled control |

HeV FC2 and NiV FC1 could inhibit both HeV and NiV-mediated fusion in a dose dependent manner and was completely inhibitory in the nM range, with $IC_{50}$ values between 5.2 and 5.8 nM, respectively. The ScHeV FC2 had no inhibitory effect on HeV or NiV-fusion. These data indicate that both viruses have a similar mechanism of fusion, that is likely comparable to that proposed for other viral systems where a trimer of hairpins has been hypothesized to form. There were no significant differences in the ability of HeV FC2 and NiV FC1 to neutralize either HeV or NiV-mediated fusion. The conservative Y450F or K479R substitutions of NiV F did not affect the ability of NiV FC1 to inhibit HeV fusion or the ability of HeV FC2 to inhibit NiV fusion. These results are further supported by helical wheel analysis which revealed that none of these amino acids fall in the proposed functional points of the putative C-terminal α-helix of HeV and NiV F thought to be involved in protein-protein interactions leading to the formation of the trimer-of-hairpin fusogenic conformation. Thus, a single heptad peptide could be used to inhibit the fusion of either virus.

In addition, the HeV-FC1 peptide has been evaluated as an inhibitor of live HeV infection under BSL4 containment. Shown in Table 2 and 3, are results obtained with the HeV-FC1 peptide inhibition of live HeV and NiV infection of Vero cells. In these experiments, 44 and 49 foci forming units (infectious units) of HeV and NiV respectively were mixed for 30 minutes with peptide at the concentrations given. Virus-peptide mixtures were adsorbed to monolayers of Vero cells in chamber slides for 30 minutes at room temperature. Virus-peptide mixtures were removed and medium containing the same concentration of peptide was added. After 24 hours incubation at 37° C. monolayers were fixed with methanol and removed from BSL4 containment. The number of foci of infection was determined by immunofluorescence using mono-specific rabbit anti-HeV P protein antiserum. Each focus of infection was a syncytium. The number of nuclei in each syncytium was readily determined except in the control (no peptide) where a proportion of syncytia contained over 60 nuclei per syncytium and in which the number of nuclei could not be accurately determined. At a concentration of about 3.5 μM the number of foci is approximately 50% that of the control value, a concentration quite comparable to other paramyxovirus systems using heptad peptides with live virus in a cell culture model.

TABLE 2

Inhibition of HeV Infection by Heptad Peptide FC1

| Peptide concentration | #Virus-infected foci | # Nuclei per focus/syncytium | % Inhibition of focus formation |
|---|---|---|---|
| 112 μM | 2.3 | 1.00 | 94.78 |
| 56 μM | 5.7 | 1.18 | 87.14 |

TABLE 2-continued

Inhibition of HeV Infection by Heptad Peptide FC1

| Peptide concentration | #Virus-infected foci | # Nuclei per focus/syncytium | % Inhibition of focus formation |
|---|---|---|---|
| 14 μM | 20.0 | 7.80 | 54.55 |
| 3.5 μM | 19.7 | 9.50 | 55.23 |
| 875 nM | 41.0 | 13.71 | 6.80 |
| 219 nM | 40.5 | 17.80 | 7.95 |
| 55 nM | 43.0 | 17.20 | 2.27 |
| none | 44.0 | >44 | 0.0 |

TABLE 3

Inhibition of NiV Infection by Heptad Peptide FC1

| Peptide concentration | #Virus-infected foci | # Nuclei per focus/syncytium | % Inhibition of focus formation |
|---|---|---|---|
| 112 μM | 4 | 0.25 | 91.8 |
| 56 μM | 4 | 0.75 | 91.8 |
| 14 μM | 18 | 7.5 | 63.26 |
| 3.5 μM | 19 | 8.9 | 61.2 |
| 875 nM | 37 | 15.6 | 24.5 |
| 219 nM | 38 | 17.8 | 22.4 |
| 55 nM | 56 | 28.63 | -14.28 |
| None | 49 | >55 | 0.0 |

There also was a significant reduction in the size of the syncytium, as determined by the number of nuclei even at the lowest peptide concentration tested.

Next, peptides were analyzed for their ability to prevent infection by NiV as determined by syncytia formation. Briefly, approximately 80 foci forming units (infectious units) of NiV were mixed for 30 min with peptides at the concentrations given and virus-peptide mixtures were adsorbed to monolayers of Vero cells in chamber slides for 30 min at RT. Virus-peptide mixtures were removed and medium containing the same concentration of peptide was added. After 24 hours at 37° C., monolayers were fixed with methanol and the number of foci of infection was determined by immuno-fluorescence using mono-specific anti-HeV P antiserum.

Figure 3:
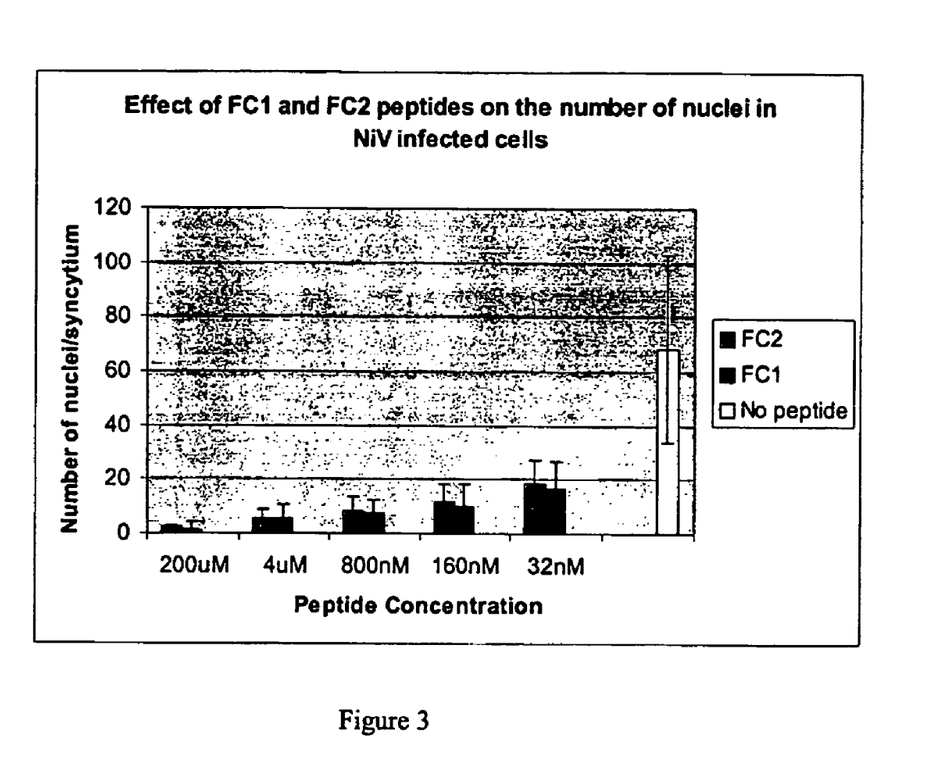
FIG. 3 A comparison of peptide concentration of FC1 or FC 2 on the number of nuclei in NiV infected cells.

As shown in FIG. 3, the number of nuclei in NiV-induced syncytia can be reduced to less than 30% of that in control untreated syncytia by both FC1 and FC2 peptides at 32 nM concentration (FIG. 2). This value approaches the $IC_{50}$ value for peptides FC1 and FC2 in the in vitro fusion assay. These data indicate that these heptad peptides may represent a therapeutic avenue for both HeV and NiV infections in humans to prevent lethal disease outcomes, such as preventing viral CNS-transition and acute encephalitic disease, and affording the infected host the an opportunity to mount a sterilizing immune response. The humoral and cellular immune responses to these viruses, like measles virus and mumps virus, which also cause systemic disease, is vigorous, potent, and capable of neutralizing low passage virus.

Taken together, in the absence of any passive or active immunization procedures or products to Nipah and Hendra virus, as well as no available anti-viral drugs for paramyxoviruses in general; the heptad peptides of the instant invention may well represent an effective therapy for Nipah and Hendra virus infection resulting from their use as a biological weapon, a natural outbreak, or a BSL4 laboratory accident. The instant heptad peptides are an effective therapeutic treatment for both Nipah and Hendra virus infection in animals, such as mammals and preferably humans, such that acute encephalitic disease or death, may be prevented. The instant heptad peptides afford the virus-infected host an opportunity to mount a sterilizing immune response.

Other embodiments and uses of the invention will be apparent to those skilled in the art from consideration of the specification and practice of the invention disclosed herein. All references cited herein for any reason, including all U.S. and foreign patents and patent applications, are specifically and entirely incorporated by reference. It is intended that the specification and examples be considered exemplary only, with the true scope and spirit of the invention indicated by the following claims.

REFERENCES

ALKHATIB, G., BRODER, C. C., and BERGER, E. A. (1996). Cell type-specific fusion cofactors determine human immunodeficiency virus type 1 tropism for T-cell lines versus primary macrophages. *J Virol* 70(8), 5487-94.

ANONYMOUS. (1999). From the Centers for Disease Control and Prevention. Outbreak of Hendra-like virus—Malaysia and Singapore, 1998-1999. *Jama* 281(19), 1787-8.

BAGAI, S., and LAMB, R. A. (1995). Quantitative measurement of paramyxovirus fusion: differences in requirements of glycoproteins between simian virus 5 and human parainfluenza virus 3 or Newcastle disease virus. *J Virol* 69(11), 6712-9.

BERGER, E. A., NUSSBAUM, O., and BRODER, C. C. (1995). HIV envelope glycoprotein/CD4 interactions: studies using recombinant vaccinia virus vectors. In "HIV: a Practical Approach, Volume II" (J. Karn, Ed.), Vol. 2, pp. 123-145. Oxford University Press, Cambridge.

BRODER, C. C., and BERGER, E. A. (1995). Fusogenic selectivity of the envelope glycoprotein is a major determinant of human immunodeficiency virus type 1 tropism for CD4+ T-cell lines vs. primary macrophages. *Proc Natl Acad Sci USA* 92(19), 9004-8.

BRODER, C. C., DIMITROV, D. S., BLUMENTHAL, R., and BERGER, E. A. (1993). The block to HIV-1 envelope glycoprotein-mediated membrane fusion in animal cells expressing human CD4 can be overcome by a human cell component (s). *Virology* 193(1), 483-91.

BRODER, C. C., and EARL, P. L. (1999). Recombinant vaccinia viruses. Design, generation, and isolation. *Mol Biotechnol* 13(3), 223-45.

BRODER, C. C., NUSSBAUM, O., GUTHEIL, W. G., BACHOVCHIN, W. W., and BERGER, E. A. (1994). CD26 antigen and HIV fusion? *Science* 264, 1156-1159.

CARROLL, M. W., and MOSS, B. (1995). *E. coli* beta-glucuronidase (GUS) as a marker for recombinant vaccinia viruses. *Biotechniques* 19(3), 352-4, 356.

CHAN, D. C., and KIM, P. S. (1998). HIV entry and its inhibition. *Cell* 93(5), 681-4.

CHUA, K. B., BELLINI, W. J., ROTA, P. A., HARCOURT, B. H., TAMIN, A., LAM, S. K., KSIAZEK, T. G., ROLLIN, P. E., ZAKI, S. R., SHIEH, W., GOLDSMITH, C. S., GUBLER, D. J., ROEHRIG, J. T., EATON, B., GOULD, A. R., OLSON, J., FIELD, H., DANIELS, P., LING, A. E., PETERS, C. J., ANDERSON, L. J., and MAHY, B. W. (2000). Nipah virus: a recently emergent deadly paramyxovirus. *Science* 288(5470), 1432-5.

CHUA, K. B., GOH, K. J., WONG, K. T., KAMARULZAMAN, A., TAN, P. S., KSIAZEK, T. G., ZAKI, S. R., PAUL, G., LAM, S. K, and TAN, C. T. (1999). Fatal encephalitis due to Nipah virus among pig-farmers in Malaysia. *Lancet* 354(9186), 1257-9.

CHUNG, M., KIZHATIL, K., ALBRITTON, L. M., and GAULTON, G. N. (1999). Induction of syncytia by neuropathogenic murine leukemia viruses depends on receptor density, host cell determinants, and the intrinsic fusion potential of envelope protein. *J Virol* 73(11), 9377-85.

DANIELS, P., KSIAZEK, T., and EATON, B. T. (2001). Laboratory diagnosis of Nipahand Hendra virus infections. *Microbes Infect* 3(4), 289-95.

DOMS, R. W., LAMB, R., ROSE, J. K., and HELENIUS, A. (1993). Folding and assembly of viral membrane proteins. *Virology* 193, 545-562.

EATON, B. T. (2001). Introduction to Current focus on Hendra and Nipah viruses. *Microbes Infect* 3(4), 277-8.

FENG, Y., BRODER, C. C., KENNEDY, P. E., and BERGER, E. A. (1996). HIV-1 entry cofactor: functional cDNA cloning of a seven-transmembrane, G protein-coupled receptor. *Science* 272(5263), 872-7.

FIELD, H., YOUNG, P., YOB, J. M., MILLS, J., HALL, L., and MACKENZIE, J. (2001). The natural history of Hendra and Nipah viruses. *Microbes Infect* 3(4), 307-14.

FUERST, T. R., NILES, E. G., STUDIER, F. W., and MOSS, B. (1986). Eukaryotic transient-expression system based on recombinant vaccinia virus that synthesizes bacteriophage T7 RNA polymerase. *Proc. Natl. Acad. Sci. USA* 83, 8122-8126.

GOH, K. J., TAN, C. T., CHEW, N. K., TAN, P. S., KAMARULZAMAN, A., SARJI, S. A., WONG, K T., ABDULLAH, B. J., CHUA, K B., and LAM, S. K. (2000). Clinical features of Nipah virus encephalitis among pig farmers in Malaysia. *N Engl J Med* 342(17), 1229-35.

GOULD, A. R. (1996). Comparison of the deduced matrix and fusion protein sequences of equine morbillivirus with cognate genes of the Paramyxoviridae. *Virus Res* 43(1), 17-31.

HALPIN, K, YOUNG, P. L., FIELD, H., and MACKENZIE, J. S. (1999). Newly discovered viruses of flying foxes. *Vet Microbiol* 68(1-2), 83-7.

HALPIN, K, YOUNG, P. L., FIELD, H. E., and MACKENZIE, J. S. (2000). Isolation of Hendra virus from pteropid bats: a natural reservoir of Hendra virus. *J Gen Virol* 81(Pt 8), 1927-1932.

HERNANDEZ, L. D., HOFFMAN, L. R., WOLFSBERG, T. G., and WHITE, J. M. (1996). Virus-cell and cell-cell fusion. *Annu Rev Cell Dev Biol* 12, 627-61.

HOOPER, P., ZAKI, S., DANIELS, P., and MIDDLETON, D. (2001). Comparative pathology of the diseases caused by Hendra and Nipah viruses. *Microbes Infect* 3(4), 315-22.

HUGHSON, F. M. (1997). Enveloped viruses: a common mode of membrane fusion? *Curr Biol* 7(9), R565-9.

HUNTER, E. (1997). Viral entry and receptors. In "Retroviruses" (S. H. Coffin, S. H. Hughes, and H. E. Varmus, Eds.), pp. 71-119. Cold Spring Harbor Laboratory Press, New York.

JIANG, S., LIN, K., STRICK, N., and NEURATH, A. R. (1993). HIV-1 inhibition by a peptide. *Nature* 365, 113.

JOSHI, S. B., DUTCH, R. E., and LAMB, R. A. (1998). A core trimer of the paramyxovirus fusion protein: parallels to influenza virus hemagglutinin and HIV-1 gp41. *Virology* 248(1), 20-34.

KLENK, H. D., and GARTEN, W. (1994). Host cell proteases controlling virus pathogenicity. *Trends Microbiol* 2(2), 39-43.

KRUEGER, D. K., KELLY, S. M., LEWICKI, D. N., RUFFOLO, R., and GALLAGHER, T. M. (2001). Variations in disparate regions of the murine coronavirus spike protein impact the initiation of membrane fusion. *J Virol* 75(6), 2792-802.

LAMB, R. A. (1993). Paramyxovirus fusion: A hypothesis for changes. *Virology* 197, 1-11.

LAMB, R. A., JOSHI, S. B., and DUTCH, R. E. (1999). The paramyxovirus fusion protein forms an extremely stable core trimer: structural parallels to influenza virus haemagglutinin and HIV-1 gp41. *Mol Membr Biol* 16(1), 11-9.

LAMB, R. A., and KOLAKOFSKY, D. (1996). Paramyxoviridae: The viruses and their replication. 3 ed. In "Virology" (B. N. Fields, D. M. Knipe, and P. M. Howley, Eds.), pp. 1177-1204. Raven Press, New York.

LEE, K. E., UMAPATHI, T., TAN, C. B., TJIA, H. T., CHUA, T. S., OH, H. M., FOCK, K. M., KURUP, A., DAS, A., TAN, A. K., and LEE, W. L. (1999). The neurological manifestations of Nipah virus encephalitis, a novel paramyxovirus. *Ann Neurol* 46(3), 428-32.

LIM, C. C., SITOH, Y. Y., HUI, F., LEE, K. E., ANG, B. S., LIM, E., LIM, W. E., OH, H. M., TAMBYAH, P. A., WONG, J. S., TAN, C. B., and CHEE, T. S. (2000). Nipah viral encephalitis or Japanese encephalitis? MR findings in a new zoonotic disease. *AJNR Am J Neuroradiol* 21(3), 455-61.

MICHALSKI, W. P., CRAMERI, G., WANG, L., SHIELL, B. J., and EATON, B. (2000). The cleavage activation and sites of glycosylation in the fusion protein of Hendra virus. *Virus Res* 69(2), 83-93.

MUNOZ-BARROSO, I., DURELL, S., SAKAGUCHI, K., APPELLA, E., and BLUMENTHAL, R. (1998). Dilation of the human immunodeficiency virus-1 envelope glycoprotein fusion pore revealed by the inhibitory action of a synthetic peptide from gp41. *J Cell Biol* 140(2), 315-23.

MURRAY, K., EATON, B., HOOPER, P., WANG, L., WILLIAMSON, M., and YOUNG, P. (1998). Flying Foxes, Horses, and Humans: a Zoonosis Caused be a New Member of the Paramyxoviridae. In "Emerging Infections" (W. M. Scheld, D. Armstrong, and J. M. Hughes, Eds.), pp. 43-58. ASM Press, Washington, D.C.

MURRAY, K., SELLECK, P., HOOPER, P., HYATT, A., GOULD, A., GLEESON, L., WESTBURY, H., HILEY, L., SELVEY, L., RODWELL, B., and ET AL. (1995). A morbillivirus that caused fatal disease in horses and humans. *Science* 268(5207), 94-7.

NANICHE, D., VARIOR-KRISHNAN, G., CERVONI, F., WILD, T. F., ROSSI, B., RABOURDIN-COMBE, C., and GERLIER, D. (1993). Human membrane cofactor protein (CD46) acts as a cellular receptor for measles virus. *J Virol* 67(10), 6025-32.

NUSSBAUM, O., BRODER, C. C., and BERGER, E. A. (1994). Fusogenic mechanisms of enveloped-virus glycoproteins analyzed by a novel recombinant vaccinia virus-based assay quantitating cell fusion-dependent reporter gene activation. *J Virol* 68(9), 5411-22.

NUSSBAUM, O., BRODER, C. C., MOSS, B., STERN, L. B., ROZENBLATT, S., and BERGER, E. A. (1995). Functional and structural interactions between measles virus hemagglutinin and CD46. *J Virol* 69(6), 3341-9.

O'SULLIVAN, J. D., ALLWORTH, A. M., PATERSON, D. L., SNOW, T. M., BOOTS, R., GLEESON, L. J., GOULD, A. R., HYATT, A. D., and BRADFIELD, J. (1997). Fatal encephalitis due to novel paramyxovirus transmitted from horses. *Lancet* 349(9045), 93-5.

PASTEY, M. K, and SAMAL, S. K. (1997). Analysis of bovine respiratory syncytial virus envelope glycoproteins in cell fusion. *J Gen Virol* 78(Pt 8), 1885-9.

PATERSON, R. G., JOHNSON, M. L., and LAMB, R. A. (1997). Paramyxovirus fusion (F) protein and hemagglutinin-neuraminidase (HN) protein interactions: intracellular retention of F and HN does not affect transport of the homotypic HN or F protein. *Virology* 237(1), 1-9.

RIMSKY, L. T., SHUGARS, D. C., and MATTHEWS, T. J. (1998). Determinants of human immunodeficiency virus type I resistance to gp41-derived inhibitory peptides. *J Virol* 72(2), 986-93.

ROOT, M. J., KAY, M. S., and KIM, P. S. (2001). Protein design of an HIV-1 entry inhibitor. *Science* 291(5505), 884-8.

Santoro, F., Kennedy, P. E., Locatelli, G., Malnati, M. S., Berger, E. A., and Lusso, P. (1999). CD46 is a cellular receptor for human herpesvirus 6. *Cell* 99(7), 817-27.

Scheid, A., and Choppin, P. W. (1974). Identification of biological activities of paramyxovirus glycoproteins. Activation of cell fusion, hemolysis, and infectivity of proteolytic cleavage of an inactive precursor protein of Sendai virus. *Virology* 57(2), 475-90.

Singh, M., Berger, B., and Kim, P. S. (1999). LearnCoil-VMF: computational evidence for coiled-coil-like motifs in many viral membrane-fusion proteins. *J Mol Biol* 290(5), 1031-41.

Skehel, J. J., and Wiley, D. C. (1998). Coiled coils in both intracellular vesicle and viral membrane fusion. *Cell* 95(7), 871-4.

Takikawa, S., Ishii, K., Aizaki, H., Suzuki, T., Asakura, H., Matsuura, Y., and Miyamura, T. (2000). Cell fusion activity of hepatitis C virus envelope proteins. *J Virol* 74(11), 5066-74.

Wang, L., Harcourt, B. H., Yu, M., Tamin, A., Rota, P. A., Bellini, W. J., and Eaton, B. T. (2001). Molecular biology of Hendra and Nipah viruses. *Microbes Infect* 3(4), 279-87.

Wang, L. F., and Eaton, B. T. (2001). Henipavirus (Paramyxoviridae). In "The Springer Index of Viruses" (C. A. Tidona, and G. Darai, Eds.), pp. In Press. Springer-Verlag, Berlin/Heidelberg.

Wang, L. F., Michalski, W. P., Yu, M., Pritchard, L. I., Crameri, G., Shiell, B., and Eaton, B. T. (1998). A novel P/V/C gene in a new member of the Paramyxoviridae family, which causes lethal infection in humans, horses, and other animals. *J Virol* 72(2), 1482-90.

Wang, L. F., Yu, M., Hansson, E., Pritchard, L. I., Shiell, B., Michalski, W. P., and Eaton, B. T. (2000). The exceptionally large genome of Hendra virus: support for creation of a new genus within the family Paramyxoviridae. *J Virol* 74(21), 9972-9.

Weissenhorn, W., Dessen, A., Calder, L. J., Harrison, S. C., Skehel, J. J., and Wiley, D. C. (1999). Structural basis for membrane fusion by enveloped viruses. *Mol Membr Biol* 16(1), 3-9.

Westbury, H. A., Hooper, P. T., Selleck, P. W., and Murray, P. K. (1995). Equine morbillivirus pneumonia: susceptibility of laboratory animals to the virus. *Aust Vet J* 72(7), 278-9.

Wild, C. T., Shugars, D. C., Greenwell, T. K., McDanal, C. B., and Matthews, T. J. (1994). Peptides corresponding to a predictive alpha-helical domain of human immunodeficiency virus type I gp41 are potent inhibitors of virus infection. *Proc Natl Acad Sci USA* 91(21), 9770-4.

Wild, T. F., and Buckland, R. (1997). Inhibition of measles virus infection and fusion with peptides corresponding to the leucine zipper region of the fusion protein. *J Gen Virol* 78(Pt 1), 107-11.

Yao, Q., Hu, X., and Compans, R. W. (1997). Association of the parainfluenza virus fusion and hemagglutinin-neuraminidase glycoproteins on cell surfaces. *J Virol* 71(1), 650-6.

Young, P. L., Halpin, K., Selleck, P. W., Field, H., Gravel, J. L., Kelly, M. A., and Mackenzie, J. S. (1996). Serologic evidence for the presence in Pteropus bats of a paramyxovirus related to equine morbillivirus. *Emerg Infect Dis* 2(3), 239-40.

Yu, M., Hansson, E., Langedijk, J. P., Eaton, B. T., and Wang, L. F. (1998a). The attachment protein of Hendra virus has high structural similarity but limited primary sequence homology compared with viruses in the genus Paramyxovirus. *Virology* 251(2), 227-33.

Yu, M., Hansson, E., Shiell, B., Michalski, W., Eaton, B. T., and Wang, L. F. (1998b). Sequence analysis of the Hendra virus nucleoprotein gene: comparison with other members of the subfamily Paramyxovirinae. *J Gen Virol* 79(Pt 7), 1775-80.

---

The invention claimed is:

1. A method for inhibiting fusion between a membrane of a Hendra or Nipah virus and a plasma membrane of a cell comprising administering to a subject in need thereof a composition comprising an effective amount of at least one polypeptide sequence consisting of SEQ ID NO: 1 or SEQ ID NO: 2 and a pharmaceutically acceptable carrier.

2. The method of claim 1, wherein said virus is Nipah virus (NiV).

3. The method of claim 1, wherein said virus is Hendra virus (HeV).

4. A method of inducing an immune response to a Hendra or Nipah virus, comprising administering to a subject in need thereof a pharmaceutically effective amount of a composition comprising at least one polypeptide selected from the group consisting of:

(a) a polypeptide consisting of SEQ ID NO: 1; and
(b) a polypeptide consisting of SEQ ID NO: 2.

5. The method of claim 4, wherein the method comprises administering a polypeptide consisting of SEQ ID NO: 1.

6. The method of claim 4, wherein the method comprises administering a polypeptide consisting of SEQ ID NO: 2.

7. The method of claim 4, wherein the subject is human.

8. The method of claim 4, wherein the composition further comprises a pharmaceutically acceptable carrier.

9. The method of claim 8, wherein the composition is formulated for oral administration, subcutaneous injection, intravenous injection, intramuscular injection, or intraperitoneal injection.

10. The method of claim 4, wherein the composition is formulated as an immunogenic composition.

11. The method of claim 4, wherein said virus is Nipah virus (NiV).

12. The method of claim 4, wherein said virus is Hendra virus (HeV).

* * * * *

SEQUENCE LISTING

```
<160> NUMBER OF SEQ ID NOS: 12

<210> SEQ ID NO 1
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Pro Val Tyr Thr Asp Lys Val Asp Ile Ser Ser Gln Ile Ser Ser
1               5                   10                  15

Met Asn Gln Ser Leu Gln Gln Ser Lys Asp Tyr Ile Lys Glu Ala Gln
            20                  25                  30

Lys Ile Leu Asp Thr Val Asn Pro Ser Leu
        35                  40

<210> SEQ ID NO 2
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 2

Pro Pro Val Phe Thr Asp Lys Val Asp Ile Ser Ser Gln Ile Ser Ser
1               5                   10                  15

Met Asn Gln Ser Leu Gln Gln Ser Lys Asp Tyr Ile Lys Glu Ala Gln
                20                  25                  30

Arg Leu Leu Asp Thr Val Asn Pro Ser Leu
            35                  40

<210> SEQ ID NO 3
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Pro Tyr Thr Gln Ser Asp Val Ser Met Ile Ser Leu Gln Ser Gln
1               5                   10                  15

Lys Ser Ile Asn Ser Leu Pro Ser Gln Ile Lys Asp Tyr Val Gln Lys
                20                  25                  30

Thr Val Ile Leu Ala Glu Asp Asn Pro
            35                  40

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Thr Ala Lys Lys Ser Lys Lys Val
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Tyr Val Thr Ala Ser Asn Glu
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Asn Leu Thr Leu Thr Leu Asn Ala
1               5

<210> SEQ ID NO 7
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 7

Ala Ala Ile Ile Val Ala Leu Ile Ala
  1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Ala Lys Asn Gln Val Gln Leu
  1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Met Asn Glu Val Glu Thr Asn Ile
  1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Val Asp Tyr Glu Glu Ser Asp Tyr
  1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Ser Ala Val Met Tyr Leu
  1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Leu Ile Leu Leu Ile
  1               5
```